United States Patent [19]

Fujita et al.

[11] Patent Number: 4,731,415

[45] Date of Patent: Mar. 15, 1988

[54] POLYISOCYANATES AND RESIN COMPOSITIONS THEREOF

[75] Inventors: Shoichi Fujita, Minoo; Kohji Nasu, Nishinomiya, both of Japan

[73] Assignee: Takeda Chemical Industries, Ltd., Osaka, Japan

[21] Appl. No.: 847,392

[22] Filed: Apr. 2, 1986

[30] Foreign Application Priority Data

Apr. 10, 1985 [JP] Japan .................................. 60-77457
Mar. 3, 1986 [JP] Japan .................................. 61-45668

[51] Int. Cl.$^4$ ............................................. C08G 18/76
[52] U.S. Cl. ........................................ 525/123; 528/67; 528/76; 528/77; 528/78; 528/80; 528/81; 528/83; 528/85; 564/38
[58] Field of Search ............................ 525/123; 564/38; 528/67, 76, 77, 78, 80, 81, 83, 85

[56] References Cited

U.S. PATENT DOCUMENTS 4,192,936  3/1980  Mohning et al. ...................... 528/67
4,613,686  9/1986  Konig et al. .......................... 564/38

FOREIGN PATENT DOCUMENTS 19273  5/1980  Japan .
95259  6/1984  Japan .

*Primary Examiner*—Maurice J. Welsh
*Attorney, Agent, or Firm*—Wenderoth, Lind & Ponack

[57] ABSTRACT

A polyisocyanate having a biuret structure obtained by allowing $\alpha,\alpha,\alpha',\alpha'$-tetramethyl-xylylene diisocyanate, a diisocyanate represented by the general formula:

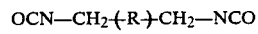

wherein R is a divalent hydrocarbon residue and water to react.

The polyisocyanate is used in the form of the two-part type of polyurethane composition in combination with a polyol.

The composition can provide coating films which excel in every physical properties required for the coating film, such as drying property, impact resistance, weathering resistance and chemical resistance, and therefore are advantageously used, for example, as a paint for automobile repairing uses, etc.

10 Claims, No Drawings

POLYISOCYANATES AND RESIN COMPOSITIONS THEREOF

This invention relates to novel fast-drying polyisocyanates and resin compositions thereof being capable of forming coating films with excellent weathering resistance, flexibility and impact resistance. In more particular, it relates to polyisocyanates and resin compositions thereof having a biuret structure which contain in the molecular structure the residues of $\alpha,\alpha,\alpha',\alpha'$-tetramethyl-xylylene diisocyanate (hereinafter referred to briefly as "TMXDI") and a diisocyanate represented by the general formula:

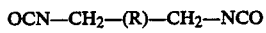

OCN—CH$_2$—(R)—CH$_2$—NCO wherein R is a divalent hydrocarbon residue.

Heretofore, polyisocyanates derived from aliphatic and alicyclic diisocyanates, because of their non-yellowing property, have been used in large quantities in various fields, such as paints and adhesives, in the form of the so-called two-part polyurethane compositions in combination with active hydrogen containing compounds, and especially find application as a paint for automobile reparing uses. Nevertheless, these diisocyanate derivatives when used solely fail to impart satisfactory drying property and impact resistance, and as a measure of improving such defect, therefore, there has been proposed a method (Japanese Patent Publication No. 19273/1980) of using as an isocyanate component mixtures formed by blending a urethane polyisocyanate derived from isophorone diisocyanate, (hereinafter referred to briefly as "IPDI"), an alicyclic diisocyanate, with a urethane polyisocyanate derived from hexamethylene diisocyanate (hereinafter referred to briefly as "HDI"), an aliphatic diisocyanate. Yet, the method is found to fail to satisfy all the requirements for the coating film, such as dyring property and impact resistance.

On the other hand, there has also been proposed a method (Japanese Unexamined Patent Publication No. 95259/1984) of using as an isocyanate component biuret type polyisocyanates containing the residues derived from IPDI and HDI in the molecular structure as formed by reacting a diisocyanate component consisting of IPDI and HDI with water, a biuret producting agent, but the method is regarded as unsatisfactory in terms of drying property and chemical resistance of the resulting coating film.

In view of the circumstances as mentioned above, the present inventors conducted research on the isocyanate component which can meet all the requirements for the coating film, such as drying property, mechanical properties, weathering resistance and chemical resistance, and as a result, found that the polyisocyanates having a biuret structure in part of the molecular structure and which contain the residue derived from TMXDI when utilized as an isocyanate can produce satisfactory results. This finding has led to the completion of this invention.

Thus, the principal object of this invention is to provide polyisocyanates having a biuret structure obtained by allowing TMXDI, a diisocyanate represented by the general formula:

OCN—CH$_2$(R)CH$_2$—NCO wherein R is a divalent hydrocarbon residue and water to react.

Another object of this invention is to provide resin compositions comprising the above polyisocyanates.

TMXDI which is usable in this invention includes, for example, m-TMXDI, p-TMXDI and mixtures thereof. These have the following structural formulae and are produced by the methods described for example in U.S. Pat. Nos. 3,290,350, 4,130,577 and 4,439,616.

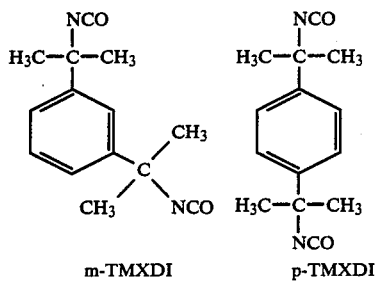

m-TMXDI     p-TMXDI

The diisocyanate represented by the above-described formula which is used in this invention is those of the formula wherein R is a divalent hydrocarbon residue, for example having 1–12 carbon atoms, as represented for example by

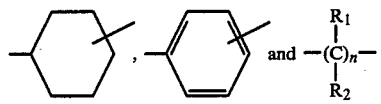

wherein R$_1$ and R$_2$ are the same or different and represent independently hydrogen or methyl group and n is an integer of 1 to 10, and its specific examples include cycloalkylene diisocyanates in which "cycloalkylene moiety" has 3–8 carbon atoms, such as 1,4-bis-(isocyanatomethyl)cyclohexane and 1,3-bis-(isocyanatomethyl)cyclohexane; aromatic-aliphatic diisocyanates in which "aliphatic moiety" has 2–6 carbon atoms, such as $\omega,\omega'$-diisocyanato-1,3-dimethylbenzene, $\omega,\omega'$-diisocyanato-1,4-dimethylbenzene and $\omega,\omega'$-diisocyanato-1,4-diethylbenzene; and aliphatic diisocyanates, such as trimethylene diisocyanate, tetramethylene diisocyanate, hexamethylene diisocyanate, pentamethylene diisocyanate, 2,4,4- or 2,2,4-trimethylhexamethylene diisocyanate and dodecamethylene diisocyanate.

In this invention, TMXDI and a diisocyanate represented by the above-described general formula are allowed to react with water to give a polyisocyanate having a biuret structure.

The formulating ratio of TMXDI to a diisocyanate represented by the above-described general formula is, in terms of molar ratio, in the range of about 95/5 to 10/90, preferably in the range of about 90/10 to 20/80. The proportion in which the mixed diisocyanate is used is not less than 3 moles of the mixed diisocyanate per mole of water, normally in the range of 4 to 30 moles, preferably in the range of 5 to 20 moles.

The reaction temperature ranges from about 50° to 200° C. The reaction temperature of less than 50° C. results in slowed reaction rate, whereas the reaction temperature in excess of 200° C. brings about an increase in molecular weight, together with exceeding coloration, thus in some instances failing to produce the polyisocyanate of commercial value.

The reaction time is normally in the range of about 1 to 5 hours, although it varies depending upon the kind and formulating ratio of the diisocyanate employed. With reference to the method of reacting water with the diisocyanate, two kinds of the diisocyanates may be mixed with water from the beginning, followed by heating up to the reaction temperature, and alternatively, TMXDI and water may be blended and heated at the reaction temperature in advance, followed by addition of other diisocyanate.

The above reaction can be carried out in the absence of solvent, but hydrophilic organic solvents, such as esters exemplified by methyl cellosolve ® acetate and cellosolve ® acetate, ketones exemplified by methyl isobutyl ketone and cyclohexanone, phosphoric acid esters exemplified by trimethyl phosphate, amides exemplified by dimethylformamide and dimethylacetamide, nitriles exemplified by propionitrile and adiponitrile and ethers exemplified by diethylene glycol dimethyl ether, may be added, solely or as a mixture of not less than two kinds thereof, to the reaction system.

For the purpose of allowing the biuret production reaction to proceed more smoothly, the surface active substances to be described below can also be used. As the surface active substance, there can be used anionic surface active agents, such as fatty acid salts, sulfates of higher alcohols, sulfates of liquid fats and oils, sulfates of aliphatic amines and aliphatic amides, phosphoric acid esters of aliphatic alcohols, sulfonates of dibasic fatty acid esters, sulfonates of aliphatic amides, alkyl aryl sulfonates, and formalin-condensed naphthalenesulfonates; cationic surface active agents, such as aliphatic amine salts, quaternary ammonium salts and alkyl pyridinium salts; nonionic surface active agents, such as polyoxyethylene alkyl ethers, polyoxyethylene alkylphenol ethers, polyoxyethylene alkyl esters, sorbitan alkyl esters and polyoxyethylene sorbitan alkyl esters; amphoteric surface active agents, such as alkylbetaines; or distanoxanes represented by the following formula and other organic tin compounds, as well.

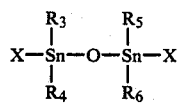

wherein $R_3$, $R_4$, $R_5$ and $R_6$ are the same or different, and represent independently an alkyl group having 1 to 6 carbon atoms; X is the same or different halogen atom, hydroxyl group, alkoxy group having 1 to 6 carbon atoms or acyloxy group having 2 to 4 carbon atoms.

The amount of the surface active substance to be used is in the range of about 0.0001 to 5 weight % against the diisocyanate mixture, preferably in the range of about 0.001 to 0.1 weight %, varying depending upon its type.

After the conclusion of the biuret production reaction, the excessive diisocyanate and hydrophilic organic solvent are removed by the known procedure, such as distillation and extraction.

In order to prevent polymerization and coloration of the organic polyisocyanates, treatment at lowered temperatures is desirable. From this standpoint, the extraction method is preferable, and in the case of treatment by means of the distillation method, it is preferred to employ a wiped film distillation apparatus.

In these production steps, there may be added, for example, coloration inhibitors, polymerization inhibitors, ultraviolet absorbers, catalysts, etc.

The thus-obtained polyisocyanate having a biuret structure from TMXDI and a diisocyanate represented by the above-described general formula preferably shows a proportion in molar ratio of the former to second diisocyanate residues in the range of about 80/20 to 20/80, particularly in the range of about 70/30 to 30/70.

The polyisocyanate possesses a chemical structure being exemplified by the following:

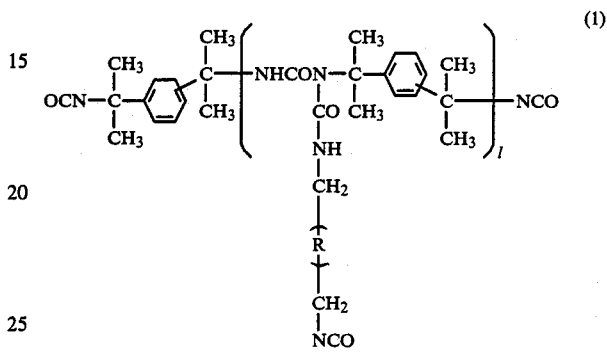

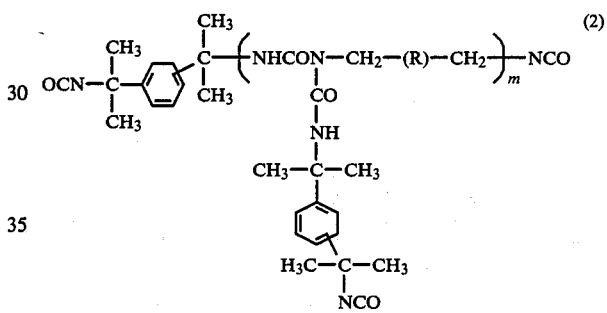

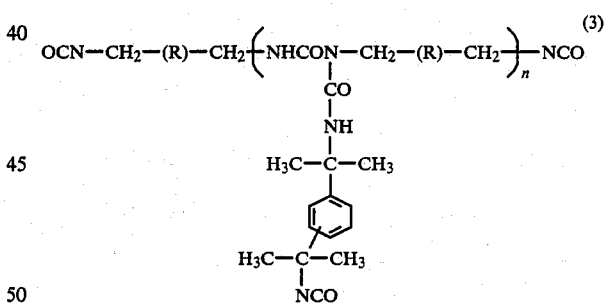

wherein R is as defined hereinbefore; l, m and n are independently an integer of 1, 2, 3, 4 and 5.

The principal constituents of the polyisocyanate having a biuret structure according to this invention are the polyisocyanates of the above-described formulae (1), (2) and (3) wherein l, m and n are independently 1, the ratios of the trimers being 30 to 70% (calculated from the surface area ratio of data by the analysis of gel permeation chromatography) and the remainder being shared by the polymers wherein l, m and n are independently not less than 2.

The polyisocyanate thus obtained, often, is used in the form of a solution in organic solvent not having hydrogen active to the NCO group in order to improve the processability. As such organic solvent, there can be utilized ester solvents, such as ethyl acetate, n-butyl acetate and isobutyl acetate; ether ester solvents, such as 2-ethoxyethyl acetate; aromatic hydrocarbon solvents, such as toluene and xylene; ketone solvents, such as methyl ethyl ketone, methyl isobutyl ketone and cyclohexanone, and the like.

The polyisocyanate is used for paints, adhesives, etc. in the form of the so-called two-part type of polyurethane composition in combination with the known active-hydrogen containing compounds, especially polyols. The polyol includes, for example, acrylic polyols, polyester polyols, polyether polyols and polyether ester polyols, and among others, acrylic polyols are preferable. The acrylic polyols include, for example, those having a molecular weight of 1,000 to 100,000 and hydroxyl value of 20 to 200, particularly 60 to 120. Such acrylic polyols are obtained by copolymerizing hydroxyl-containing monomers, such as 2-hydroxyethyl methacrylate, 2-hydroxypropyl methacrylate, 2-hydroxyethyl acrylate, hydroxypropyl acrylate and N-methylolacrylamide, with other monomers, such as styrene, methyl methacrylate, ethyl methacrylate, n-butyl methacrylate, isobutyl methacrylate, tert-butyl methacrylate, acrylonitrile, methacrylonitrile, methyl acrylate, ethyl acrylate, n-butyl acrylate, isobutyl acrylate, tert-butyl acrylate, 2-ethylhexyl acrylate and 2-ethylhexyl methacrylate. Such acrylic polyols may be those formed by copolymerizing the above monomers furthermore, if desired, with amino-containing monomers, such as 2-diethylaminoethyl methacrylate and tert-butylaminoethyl methacrylate, glycidyl-containing monomers, such as glycidyl acrylate and glycidyl methacrylate, amide-containing monomers, such as acrylamide and methacrylamide, acid-containing monomers, such as acrylic acid, methacrylic acid, maleic anhydride, crotonic acid, fumaric acid and itaconic acid, and further fumarates, itaconates, etc.

When the acrylic polyol shows a molecular weight of below 1,000, the resulting coating film exhibits decreased physical properties, such as flexibility, weathering resistance and chemical resistance, and when its molecular weight is more than 100,000, there results in increased viscosity, thus causing sometimes deteriorated paintability. When it shows a hydroxyl value of less than 20, the resulting coating film demonstrates deteriorated chemical resistance, and in the case of the hydroxyl value of more than 200, deterioration in flexibility, impact resistacne and adherence is sometimes caused.

Examples of the polyester polyol include reaction products of polyhydric alcohols and polybasic acids. The polyhydric alcohols include, for example, ethylene glycol, propylene glycol, butylene glycol, hexylene glycol, neopentyl glycol, cyclohexanedimethanol, diethylene glycol, triethylene glycol, polyethylene glycol, dipropylene glycol, polyoxypropylene glycol, polyoxybutylene glycol, glycerol, trimethylolpropane, pentaerythritol, and sorbitol. As the polybasic acids, there can be mentioned succinic acid, adipic acid, azelaic acid, sebacic acid, phthalic acid, isophthalic acid, terephthalic acid, tetrahydrophthalic acid, hexahydrophthalic acid, maleic acid, fumaric acid and these acid anhydrides. Also, polyester polyols formed by allowing lactones, such as caprolactone and methylcaprolactone, to undergo ring-opening polymerization are preferred examples.

Examples of the polyether polyols include polyols formed by polymerizing epoxide compounds, such as ethylene oxide, propylene oxide, butylene oxide, tetrahydrofurane, styrene oxide, epichlorohydrin, phenyl glycidyl ether and allyl glycidyl ether, in the presence of catalyst, for example, boron trifluoride as well as those which can be produced by allowing these epoxides, solely or as a mixture, to undergo addition to an initiator containing reactive hydrogen atoms. The initiator containing reactive hydrogen atoms includes, for example, water, polyols, such as ethylene glycol, propylene glycol, glycerol, tirmethylolpropane, pentaerythritol and sorbitol, aminoalcohols, such as ethanolamine, and polyamines, such as ethylenediamine.

Examples of the polyether ester polyols include those obtained by subjecting the above-described polyethers used as a starting material and plybasic acids to a polyesterification reaction as well as compounds having both polyether and polyester segments in the molecule formed through a ring-opening copolymerization reaction of epoxide compounds with acid anhydride.

The formulating ratio of the above-described isocyanate to OH components is preferably about 0.2 to 3.0, particularly about 0.7 to 1.5 of the NCO/OH equivalent ratio.

Though the composition, as such, can be used as a clear varnish, adhesive, etc., they may be incorporated with coloring pigments or fillers, such dispersing agents as those based on silicone, amine, polyether, polyester, castor oil, synthetic wax and bentonite, defoaming agents, levelling agents, thixotropic agents, such stabilizers as those based on benzotriazole, hindered amine and hindered phenol, such reaction catalysts as those based on tin, lead, zinc and iron, and the like.

Application is normally carried out by the use of air spray gun, airless spray gun, etc., and can also be conducted by means of brush, roll coater, flow coater, dipping, electrostatic coating, etc.

Although TMXDI to be used in this invention, itself, is not readily susceptible to biuret conversion owing to its chemical structure as described above through steric hindrance of the methyl group, its combined use with the diisocyanate represented by the above general formula can facilitate the production of the polyisocyanate having a biuret structure of TMXDI and the diisocyanate of the above general formula.

In addition, the two-part polyurethane compositions derived from the polyisocyanate used as an isocyanate component can provide coating films which excel in every physical properties required for the coating film, such as drying property, impact resistance, weathering resistance and chemical resistance, and therefore are advantageously used, for example, as a paint for automobile repairing uses, etc.

The examples are described below to illustrate this invention more specifically.

EXAMPLE 1

Charged in a reaction vessel were 1161 g (4.75 moles) of m-TMXDI, 42 g (0.25 mole) of hexamethylene diisocyanate, 9 g (0.5 mole) of water and 360 g of trimethyl phosphate, and the reaction was allowed to proceed at 140° C. for 3 hours.

The reaction solution was placed in a wiped film distillation apparatus, and the unreacted diisocyanate and trimethyl phosphate were removed under the conditions of 0.3 mmHg and 170° C. to give a yellowish, clear solid reaction product.

The product was found to show an NCO content of 15% and viscosity (at 25° C., as a 75% butyl acetate solution) of 6700 cps. The infrared absorption spectrum of the product with the absorptions observed at 1680 cm$^{-1}$ and 1640 cm$^{-1}$ indicated that it has a biuret structure.

From the fact that the product shows a molar ratio of m-TMXDI to HDI of about 3.5/1.5, it is assumed to be be composed principally of the substance having the following structure.

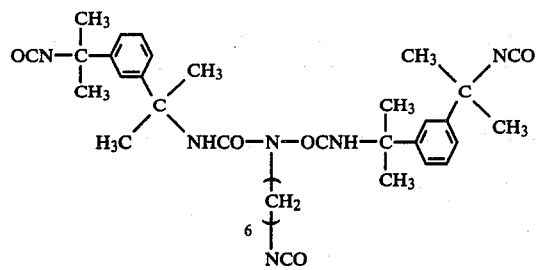

The ratio of the principal constituent in the product was found to be about 40%.

EXAMPLES 2 to 5

By varying the ratio of m-TMXDI to HDI, the reactions were carried out under conditions as shown in Table 1 similar to those of Example 1. The reaction solutions were treated in a wiped film distillation apparatus under the conditions of 0.3 mmHg and 170° C., and the resulting reaction products are presumed to be composed principally of the compound having the following structure. The proportions of the principal components in the products are as follows:

EXAMPLE 2

The principal component shows the same structure as that of Example 1, and its proportion was found to be 42%.

EXAMPLE 3

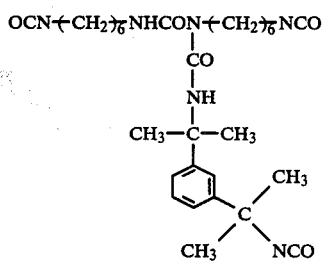

The ratio of the principal constituent was found to be 45%.

EXAMPLE 4

The principal constituent shows the same structure as that of Example 3, and its ratio was found to be 55%.

EXAMPLE 5

The principal constituent shows the same structure as that of Example 3, and its ratio was found to be 60%.

The reaction products as obtained in Examples 2 to 5 exhibited physical properties as shown in Table 1.

EXAMPLE 6

Charged in a reaction vessel were 1222 g (5 moles) of m-TMXDI, 9 g (0.5 mole) of water, 0.024 g of dibutyltin dilaurate and 360 g of trimethyl phospahte, and the reaction was allowed to proceed at 70° C. for 1 hour. 168 g (1 mole) of HDI was added to the reaction mixture, and the reaction was allowed to proceed at 140° C. for 3 hours.

The reaction solution was treated in a wiped film distillation apparatus, and the infrared absorption spectrum of the resulting product revealed the absorptions at 1680 cm$^{-1}$ and 1640 cm$^{-1}$. The principal constituent of the product was found to have the same structural formula as that of the reaction product of Example 1, with its ratio being 40%.

COMPARATIVE EXAMPLE 1

Charged in a reaction vessel were 1222 g (5 moles) of TMXDI, 9 g (0.5 mole) of water, 0.024 g of dibutyltin dilaurate and 400 g of trimethyl phosphate, and the reaction was allowed to proceed at 140° C. for 5 hours. The reaction product obtained after the treatment of the reaction solution showed the infrared absorption spectrum revealing the absorption only at 1640 cm$^{-1}$ (urea linkage), and was not found to possess a biuret structure.

COMPARATIVE EXAMPLE 2

Allowed to undergo a reaction at 140° C. for 3 hours 841 g (5 moles) of HDI, 9 g (0.5 mole) of water and 250 g of trimethyl phosphate and the reaction solution was subjected to distillation treatment. The resulting reaction product showed an NCO content of 23.3% and viscosity (at 25° C., as a 75% butyl acetate solution) of 70 cps.

COMPARATIVE EXAMPLE 3

A 50/50 (on a weight basis) mixture of the product of Comparative Example 2 and a prepolymer (with an NCO content of 10.5% and solid content of 75%: Takenate ® D-140N, produced by Takeda Chemical Industries, Ltd. of Japan) of IPDI and trimethylolpropane.

The coating films derived from the products as obtained in Examples 1 to 6 and Comparative Examples 2 and 3 and an acrylic polyol (Acridick ® A-801, produced by Dai-Nippon Ink & Chemicals of Japan) at an NCO/OH ratio=1.0 showed physical properties as shown in Table 1, the lower section, respectively.

TABLE 1

| Example | | 1 | 2 | 3 | 4 | 5 | 6 | Comparative Example 2 | Comparative Example 3 |
|---|---|---|---|---|---|---|---|---|---|
| Biuret production reaction | TMXDI mole | 4.75 | 4.5 | 4 | 3.5 | 2.5 | 5 | | Reaction Product of Comparative Example 2/ IPDI-TMP prepolymer 50/50 parts |
| | HDI mole | 0.25 | 0.5 | 1 | 1.5 | 2.5 | 1 | 5 | |
| | H$_2$O mole | 0.5 | 0.5 | 0.5 | 0.5 | 0.5 | 0.5 | 0.5 | |
| Reaction product | TMXDI mole | 3.5 | 3 | 2 | 1.5 | 1 | 2.8 | 0 | |

TABLE 1-continued

| Example | | 1 | 2 | 3 | 4 | 5 | 6 | Comparative Example 2 | Comparative Example 3 |
|---|---|---|---|---|---|---|---|---|---|
| | HDI mole | 1.5 | 2 | 3 | 3.5 | 4 | 2.2 | 10 | |
| | NCO content (%) | 15.0 | 15.8 | 16.7 | 18.4 | 21.5 | 15.0 | 23.3 | |
| | Viscosity 25° C., CPS (75% BA solution) | 6700 | 4500 | 1000 | 500 | 200 | 2200 | 70 | |
| (Physical properties of the coating film) Curing time (JIS K5400 hr.: min.) | | 2:00 | 2:20 | 3:10 | 4:30 | 7:20 | 2:30 | 9:00 | 1:20 |
| Erichsen cupping test (mm) | | 8 | 8 | 8 | 8 | 8 | 8 | 8 | 3 |
| Impact test (Dupont, 1/2φ, g × cm) | | 500 × 50 | 500 × 50 | 500 × 50 | 500 × 50 | 500 × 50 | 500 × 50 | 500 × 50 | 300 × 40 |
| Bending test (Bending tester, mmφ) | | 2 | 2 | 2 | 2 | 2 | 2 | 2 | 8 |

EXAMPLE 7

A 732 g (3 moles) quantity of m-TMXDI, 420 g (2 moles) of 2,2,4-trimethylhexamethylene diisocyanate, 9 g (0.5 mole) of water and 360 g of trimethyl phosphate were allowed to undergo a reaction at 150° C. for 3 hours. The reaction solution was subjected to a wiped film distillation apparatus, and the resulting reaction product showed an NCO content of 16.5% and viscosity (at 25° C., as a 75% butyl acetate solution) of 1200 cps.

From a molar ratio of m-TMXDI to 2,2,4-trimethyl-hexamethylene diisocyanate of about 2/3, it is assumed that the product is composed principally of the following:

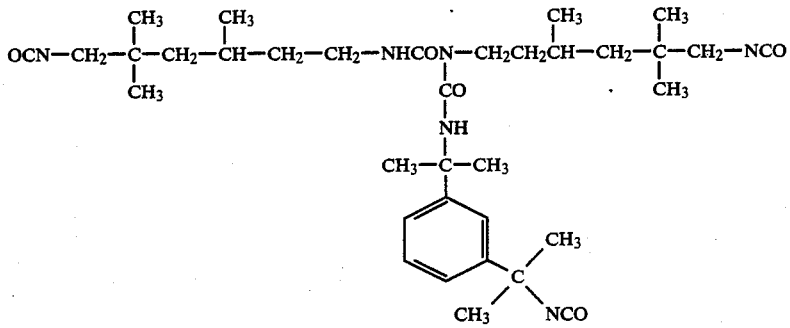

The ratio of the principal constituent was found to be 50%.

The reaction product, when it was reacted with an acrylic polyol in a manner simlar to those of Examples 1 to 6, provided a coating film with the following physical properties:
  Drying property: 3 hours 40 minutes
  Erichsen: 8 mm
  Impact resistance: (½φ): 500 g×50 cm
  Bending test: 2 mm

EXAMPLE 8

A 732 g (3 moles) quantity of m-TMXDI, 388 g (2 moles) of 1,3-bis(isocyanatomethyl)cyclohexane, 9 g (0.5 mole) of water and 360 g of trimethyl phosphate were allowed to undergo a reaction at 150° C. for 3 hours. The reaction solution was subjected to a wiped film distillation apparatus and the reaction product was confirmed to have a biuret structure by measuring the infrared absorption spectrum.

The product showed an NCO content of 15.8% and viscosity (at 25° C., as a 75% butyl acetate solution) of 4500 cps. Its principal constituent is presumed to be:

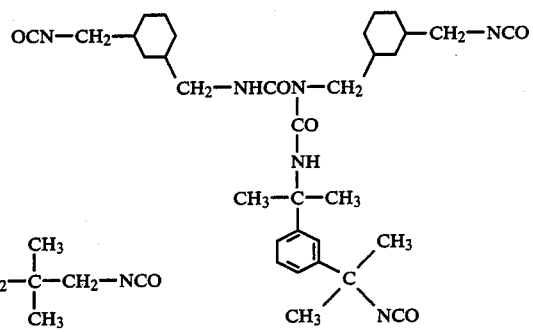

The ratio of the principal constituent was found to be 58%.

The above reaction product, when it was used in combination with an acrylic polyol in a manner similar to those of Examples 1 to 6, provided a coating film with the following physical properties:
  Drying property: 2 hours 10 minutes
  Erichsen: 8 mm
  Impact resistance (½φ): 500 g×40 cm Bending test 3 mm

EXAMPLE 9

A 732 g (3 moles) quantity of m-TMXDI, 376.4 g (2 moles) of ωω'-diisocyanato-1,3-dimethyl benzene, 9 g (0.5 mole) of water and 340 g of trimethyl phosphate were allowed to undergo a reaction at 150° C. for 3.5 hours.

The reaction solution was subjected to a wiped film distillation apparatus and the reaction product was confirmed to have a biuret structure by measuring the infrared absorption spectrum.

The product showed an NCO content of 16.1% and viscosity (at 25° C., as a 75% butyl acetate solution) of 3,800 cps.

Its principal constituent is presumed to be:

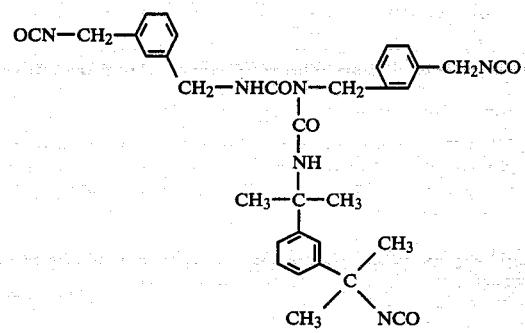

The ratio of the principal constituent was found to be 59%.

The above reaction product, when it was used combination with an acrylic polyol in a similar to those of Examples 1 to 6, provided a coating film with the following physical properties:

Drying property: 55 minutes
Erichsen: 8 mm
Impact resistance: (½φ) 500g×50 cm
Bending test 2 mm

What is claimed is:

1. A polyisocyanate having a biuret structure obtained by allowing α,α, α',α'-tetramethyl-xylene diisocyanate, a diisocyanate represented by the general formula:

OCN—CH$_2$—(R)—CH$_2$—NCO wherein R is a divalent hydrocarbon residue having 1-12 carbon atoms and water to react.

2. The polyisocyanate as claimed in claim 1, wherein R is a divalent hydrocarbon residue represented by

wherein R$_1$ and R$_2$ are the same or different and represent independently hydrogen or methyl group and n is an integer of 1 to 10.

3. The polyisocyanate as claimed in claim 1, wherein the formulating ratio of α,α,α',α'-tetramethyl-xylene diisocyanate to the diisocyanate represented by the general formula is, in terms of molar ratio, in the range of about 95/5 to 10/90.

4. The polyisocyanate as claimed in claim 1, wherein the proportion in which the mixed diisocyanate is used is not less than 3 moles of the mixed diisocyanate per mole of water.

5. The polyisocyanate as claimed in claim 1, wherein the reaction temperature is in the range of about 50° to 200° C.

6. The polyisocyanate as claimed in claim 1, wherein the reaction is carried out in the presence of a hydrophilic organic solvent.

7. The polyisocyanate as claimed in claim 1, wherein the reaction is carried out in the presence of a surface active substance.

8. The polyisocyanate as claimed in claim 1, wherein its principal constituents are ones represented by the formulae

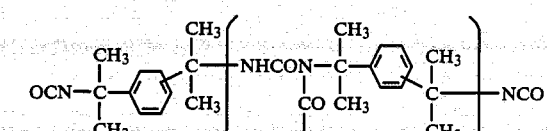

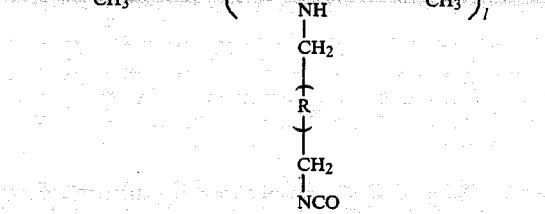

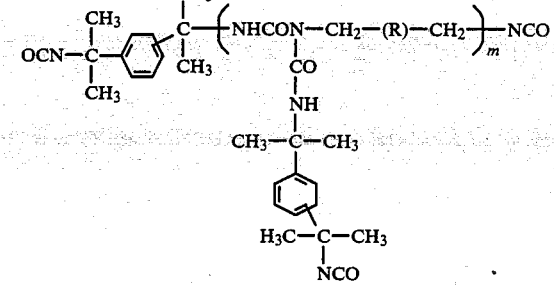

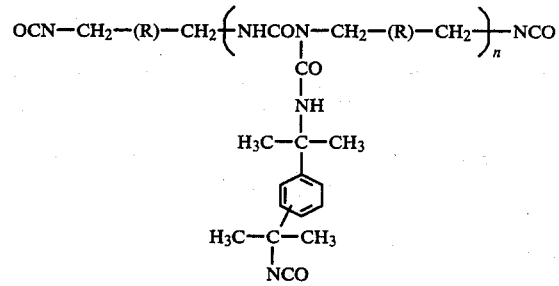

wherein R is a divalent hydrocarbon residue and l, m and n are independently 1, the ratios of the principal constituents being in the range of 30 to 70%.

9. A resin composition which comprises (1) a polyisocyanate having a biuret structure obtained by allowing α,α,α',α'-tetramethyl-xylylene diisocyanate, a diisocyanate represented by the general formula:

OCN—CH$_2$—(R)—CH$_2$—NCO wherein R is a divalent hydrocarbon residue having 1-12 carbon atoms and water to react and (2) a polyol.

10. The resin composition as claimed in claim 9, wherein the formulating ratio of the polyisocyanate to the polyol is about 0.2 to 3.0 of the NCO/OH equivalent ratio.

* * * * *